(12) United States Patent
Mark

(10) Patent No.: US 8,433,391 B2
(45) Date of Patent: Apr. 30, 2013

(54) SITE MARKER

(75) Inventor: Joseph L. Mark, Indianapolis, IN (US)

(73) Assignee: Suros Surgical Systems, Inc., Indianapolis, IN (US)

(*) Notice: Subject to any disclaimer, the term of this patent is extended or adjusted under 35 U.S.C. 154(b) by 170 days.

(21) Appl. No.: 12/269,501

(22) Filed: Nov. 12, 2008

(65) Prior Publication Data

US 2009/0069670 A1    Mar. 12, 2009

Related U.S. Application Data

(63) Continuation-in-part of application No. 10/964,087, filed on Oct. 13, 2004, now abandoned.

(51) Int. Cl.
*A61B 5/05*     (2006.01)

(52) U.S. Cl.
USPC ............ 600/414; 600/420; 600/426; 600/431

(58) Field of Classification Search .................. 600/431, 600/414, 420, 426
See application file for complete search history.

(56) References Cited

U.S. PATENT DOCUMENTS

| | | | |
|---|---|---|---|
| 5,010,145 A | 4/1991 | Ikada et al. | |
| 5,104,539 A | 4/1992 | Anderson et al. | |
| 5,693,085 A | 12/1997 | Buirge et al. | |
| 6,347,241 B2 | 2/2002 | Burbank et al. | |
| 6,350,244 B1 | 2/2002 | Fisher | |
| 6,379,379 B1 | 4/2002 | Wang | |
| 7,074,189 B1* | 7/2006 | Montegrande | 600/462 |
| 7,611,462 B2 | 11/2009 | Vortman et al. | |
| 2001/0049549 A1 | 12/2001 | Boylan et al. | |
| 2002/0035324 A1* | 3/2002 | Sirimanne et al. | 600/431 |
| 2002/0188196 A1 | 12/2002 | Burbank et al. | |
| 2003/0097059 A1* | 5/2003 | Sorrell et al. | 600/420 |
| 2004/0030262 A1 | 2/2004 | Fisher et al. | |
| 2004/0093069 A1 | 5/2004 | Priewe et al. | |
| 2004/0110059 A1 | 6/2004 | Onishi et al. | |
| 2004/0116806 A1* | 6/2004 | Burbank et al. | 600/431 |
| 2004/0138555 A1 | 7/2004 | Krag et al. | |
| 2004/0219186 A1* | 11/2004 | Ayres | 424/426 |
| 2005/0033157 A1* | 2/2005 | Klein et al. | 600/411 |
| 2005/0063908 A1* | 3/2005 | Burbank et al. | 424/9.5 |
| 2005/0288764 A1 | 12/2005 | Snow et al. | |
| 2007/0118176 A1 | 5/2007 | Opolski et al. | |
| 2007/0167980 A1 | 7/2007 | Figulla et al. | |
| 2008/0058715 A1 | 3/2008 | Houser et al. | |

FOREIGN PATENT DOCUMENTS

| | | |
|---|---|---|
| EP | 1 602 341 A1 | 12/2005 |
| EP | 1 925 266 A2 | 5/2008 |
| WO | WO-01/00101 A1 | 1/2001 |

OTHER PUBLICATIONS

Final Office Action dated Feb. 16, 2010 for U.S. Appl. No. 10/964,087.
Response to Final Office Action dated Feb. 16, 2010 for U.S. Appl. No. 10/964,087.

(Continued)

*Primary Examiner* — Unsu Jung
*Assistant Examiner* — Saurel J Selkin
(74) *Attorney, Agent, or Firm* — Vista IP Law Group LLP

(57) ABSTRACT

A site marker and method of using a site marker are described and disclosed. The site marker comprises a bio-compatible and a plurality of elements, wherein the biocompatible material and at least one of the plurality of elements are imageable under different modalities.

10 Claims, 2 Drawing Sheets

OTHER PUBLICATIONS

Non-Final Office Action dated May 25, 2010 for U.S. Appl. No. 12/133,212.
Non-Final Office Action dated Jun. 8, 2010 for U.S. Appl. No. 10/964,087.
Amendment After Final Office Action filed with RCE in response to Advisory Action dated May 6, 2010 for U.S. Appl. No. 10/964,087.
Office Action dated Aug. 4, 2009 for U.S. Appl. No. 10/964,087.
Response to Office Action dated Aug. 4, 2009 for U.S. Appl. No. 10/964,087.
PCT International Search Report for PCT/US2009/046200 dated Oct. 5, 2009.
Non-Final Office Action dated Jun. 28, 2010 for U.S. Appl. No. 11/242,334.
Response to Non-Final Office Action dated May 25, 2010 for U.S. Appl. No. 12/133,212.
Response to Non-Final Office Action dated Jun. 8, 2010 for U.S. Appl. No. 10/964,087.
Response to Non-Final Office Action dated Jun. 28, 2010 for U.S. Appl. No. 11/242,334.
Final Office Action dated Nov. 23, 2010 for U.S. Appl. No. 12/133,212.
Non-Final Office Action dated Dec. 8, 2010 in U.S. Appl. No. 10/964,087.
Final Office Action dated Jan. 4, 2011 for U.S. Appl. No. 11/242,334.
Non-Final Office Action dated Dec. 27, 2010 for U.S. Appl. No. 11/561,919.
Response to Final Office Action dated Nov. 23, 2010 for U.S. Appl. No. 12/133,212.
Response to Non-Final Office Action dated Dec. 8, 2010 for U.S. Appl. No. 10/964,087.
Response to Advisory Action to Place Application in Condition for Allowance dated Feb. 3, 2011 for U.S. Appl. No. 12/133,212.
Response to Non-Final Office Action dated Dec. 27, 2010 for U.S. Appl. No. 11/561,919.
Response to Final Office Action dated Jan. 4, 2011 for U.S. Appl. No. 11/242,334.
Notice of Allowance dated May 10, 2011 for U.S. Appl. No. 12/133,212.
Final Office Action dated May 19, 2011 for U.S. Appl. No. 10/964,087.
Notice of Allowance dated Jun. 10, 2011 for U.S. Appl. No. 11/561,919.
Non-Final Office Action dated Jul. 6, 2011 for U.S. Appl. No. 11/242,334.
Non-Final Office Action dated Sep. 26, 2011 for U.S. Appl. No. 12/133,212.
Response to Non-Final Office Action dated Jul. 6, 2011 for U.S. Appl. No. 11/242,334.

* cited by examiner

SITE MARKER

CROSS-REFERENCE TO RELATED APPLICATIONS

This application is a Continuation-in-part of U.S. Ser. No. 10/964,087, filed Oct. 13, 2004, the disclosure of which is incorporated herein by reference in its entirety.

TECHNICAL FIELD

The present disclosure relates to site markers used to identify biopsy locations in a patient's anatomy, and more specifically, to radiopaque site markers that are suitable for use in magnetic resonance imaging and/or magnetic resonance spectroscopy procedures.

BACKGROUND

In the diagnosis and treatment of breast cancer, it is often necessary to perform a biopsy to remove tissue samples from a suspicious mass. The suspicious mass is typically discovered during a preliminary examination involving visual examination, palpation, x-ray, magnetic resonance imaging (MRI), ultrasound imaging or other detection means.

When a suspicious mass is detected, a sample is taken by biopsy, and then tested to determine whether the mass is malignant or benign. This biopsy procedure can be performed by an open surgical technique, or through the use of a specialized biopsy instrument. To minimize surgical intrusion, a small specialized instrument such as a biopsy needle is inserted in the breast while the position of the needle is monitored using an imaging technique such as fluoroscopy, ultrasonic imaging, x-rays, or MRI. In addition, techniques such as magnetic resonance spectroscopy (MRS) imaging may be used to assess the likelihood or extent of cancerous cell growth by determining the level of certain compounds which are indicative of cancer cells.

In a relatively new procedure, referred to as stereotactic needle biopsy, the patient lies on a special biopsy table with her breast compressed between the plates of a mammography apparatus and two separate x-rays are taken from two different points of reference. A computer then calculates the exact position of the mass or lesion within the breast. The coordinates of the lesion are then programmed into a mechanical stereotactic apparatus which advances the biopsy needle into the lesion with precision. At least five biopsy samples are usually taken from locations around the lesion and one from the center of the lesion.

Regardless of the method or instrument used to perform the biopsy, subsequent examination of the surgical site may be necessary, either in a follow up examination or for treatment of a cancerous lesion. Treatment often includes a mastectomy, lumpectomy, radiation therapy, or chemotherapy procedure that requires the surgeon or radiologist to direct surgical or radiation treatment to the precise location of the lesion. Because this treatment might extend over days or weeks after the biopsy procedure, by which time the original features of the tissue may have been removed or altered by the biopsy, it is desirable to insert a site marker into the surgical cavity to serve as a landmark for future identification of the location of the lesion.

Known biopsy site markers have been found to have disadvantages in that the site markers are not visible under all available modalities or those that are useful for diagnosing and treating the patient. Moreover, because of this problem, when cancer is found at a biopsy site that has been previously marked with a site marker, due to the poor visibility of the biopsy site marker under ultrasound or other visualization modalities, the patient must undergo an additional procedure that places an additional device at the biopsy site to enable the surgeon to find the biopsy site in subsequent procedures. Accordingly, a need has arisen for a site marker which addresses the foregoing issues.

BRIEF DESCRIPTION OF THE DRAWINGS

Embodiments of the present invention will now be described by way of example in greater detail with reference to the attached figures, in which.

DETAILED DESCRIPTION

Figure 1:
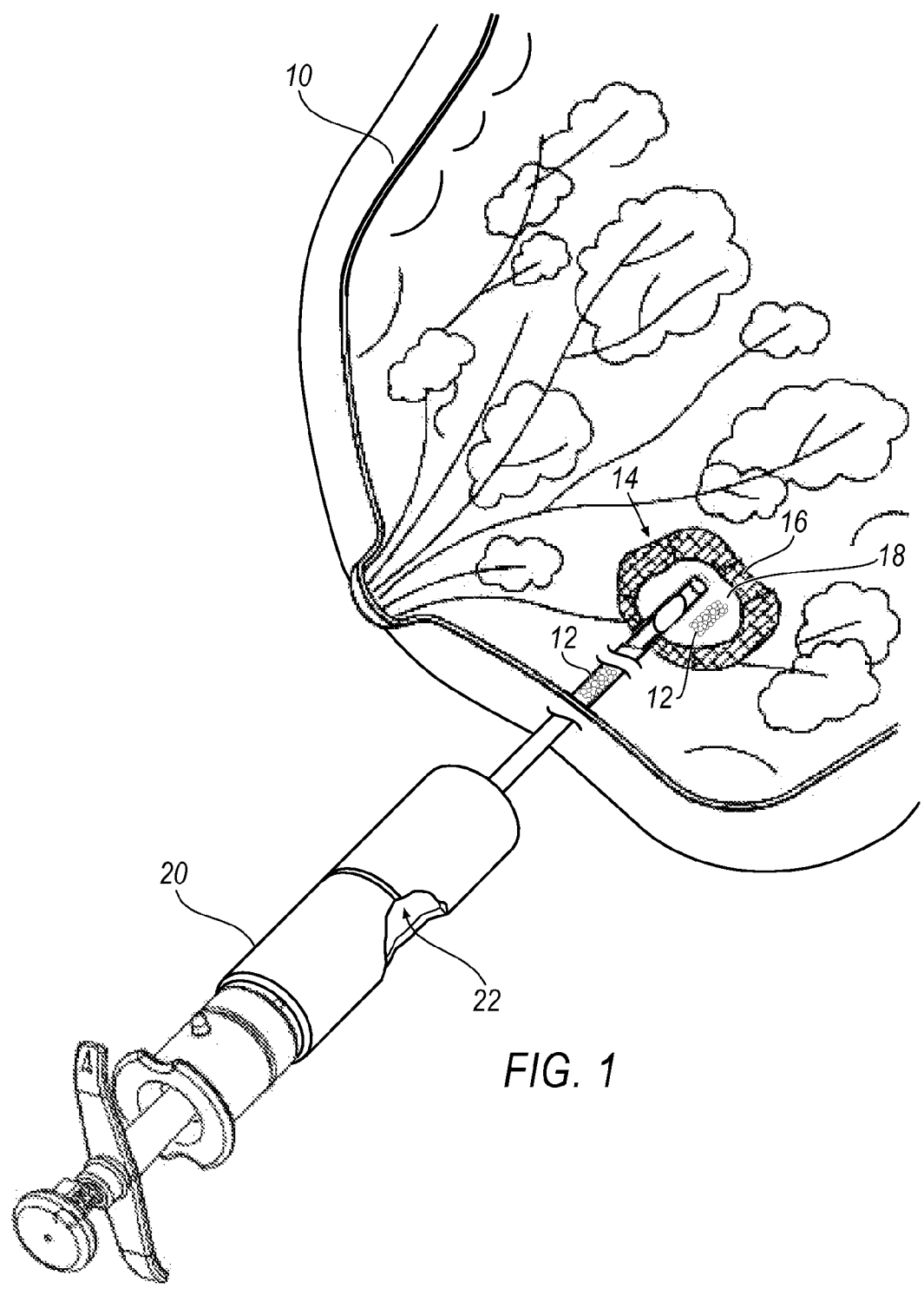
FIG. 1 is a perspective view of a biopsy site in a human breast showing the breast in section and one or more site markers being implanted in the biopsy cavity using a site marker delivery system.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present invention. Further, the descriptions set forth herein are not intended to be exhaustive or otherwise limit or restrict the claims to the precise forms and configurations shown in the drawings and disclosed in the following detailed description.

Described herein are site markers which comprise a bio-compatible material and a plurality of elements, wherein the bio-compatible material and at least one of the plurality of elements are imageable with different modalities. In one embodiment, the bio-compatible material comprises a radiopaque material that is not itself MRI-imageable, and the plurality of elements are MRI-imageable. The radiopaque material allows the site marker to be radiographically imaged using techniques such as x-ray, computed tomography (CT) scanning, fluoroscopy, etc. The MRI-imageable elements have magnetic properties that allow the site marker to be visualized under MRI. As discussed further below, in exemplary configurations the bio-compatible radiopaque site marker defines a closed solid with a hollow interior in which the MRI-imageable elements are disposed or the MRI-imageable elements are suspended in the biocompatible radiopaque material itself.

FIG. 1 illustrates a perspective view of a human breast 10 being implanted with a site marker 12. Biopsy site 14 includes lesion 16 from which a tissue sample has been removed, resulting in a biopsy cavity 18. One or more site markers 12 are implanted in the biopsy cavity 18 using a marker delivery system 20, as shown in FIG. 1. In one embodiment, the marker delivery system 20 is slidably advanced through an inner lumen 22 of a biopsy device (not shown), which avoids the need to withdraw the biopsy device and thereafter insert the marker delivery system 20. Delivering the site marker 12 in the biopsy cavity 18 without withdrawing the biopsy device reduces the amount of tissue damage and enables more accurate placement of the site marker 12. The marker delivery system 20 illustrated in FIG. 1 is exemplary only and it is understood that the site marker embodiments disclosed herein are suitable for use with other marker delivery systems.

Figure 2:
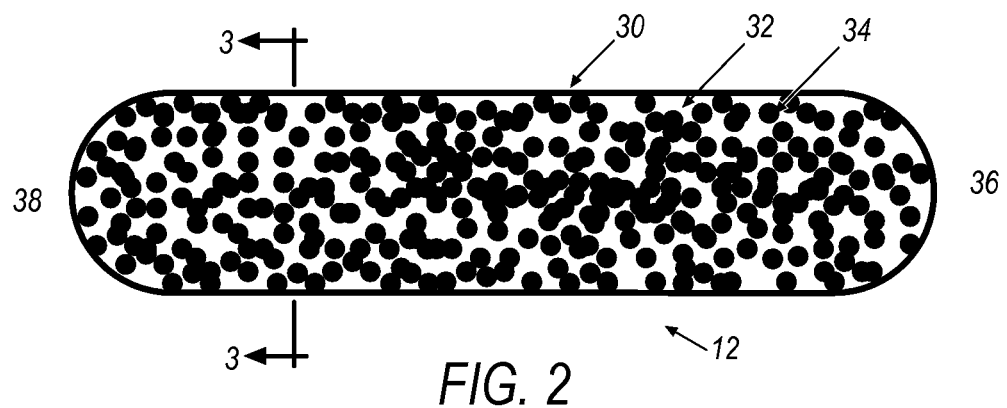
FIG. 2 is a side elevational view of a first embodiment of a site marker.

Referring to FIG. 2, site marker 12 is illustrated in greater detail. Site marker 12 comprises a radiopaque element 30 formed from a radiopaque material into a desired shape, which is a pellet in the figure. Radiopaque element 30 is also preferably biocompatible so that it does not injure or cause a toxic or immunologic reaction in the patient's tissue. In preferred embodiments, the material comprising radiopaque element 30 is non-magnetic and non-MRI imageable. In an especially preferred embodiment, radiopaque element 30 is formed from a glass material. Any known biocompatible glass may be used, including but not limited to soda-lime, lead-alkali, borosilicate, aluminosilicate, silica and fused silica.

Figure 3A:
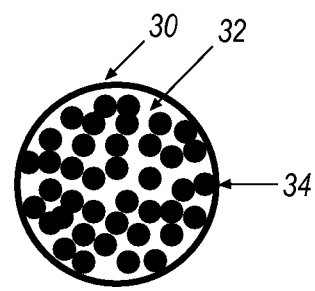
FIG. 3A is a cross-sectional view of the site marker of FIG. 2 taken along line 3-3.

Radiopaque element 30 may be solid throughout or may comprise one or more internal hollow spaces. In the embodiment of FIGS. 2 and 3A, radiopaque element 30 defines a fully, enclosed hollow internal volume 32. Radiopaque element 30 may be formed into a variety of shapes; however, those shapes that will be more readily identified and distinguished from surrounding tissue structures when imaged are preferred. In the embodiment of FIGS. 2 and 3A, radiopaque material 30 is provided in the shape of an elongated pellet. However, spherical shapes, elliptical shapes, cylindrical shapes, polyhedral shapes, and oval shapes may be used. In addition, site marker 12 may be symmetrical, asymmetrical, or have an irregular shape. Radiopaque element 30 is preferably dimensioned to be implanted using marker delivery system 20 and to be distinguishable from surrounding tissue.

Site marker 12 also preferably comprises an MRI-imageable material. In the embodiment of FIGS. 2-3A, the MRI-imageable material comprises a plurality of MRI-imageable elements 34 which are disposed in hollow space 32 of radiopaque element 30. Alternatively, MRI-imageable elements 34 may be disposed in a plurality of hollow spaces that are separated from one another within radiopaque element 30. MRI-imageable elements 34 are preferably provided in an amount that allows site marker 12 to be viewed under MRI. MRI-imageable elements 34 may be loosely or tightly packed in hollow space 32. The MRI-imageable elements 34 may have uniform or non-uniform, sizes, shapes, and/or compositions. In certain preferred embodiments, MRI-imageable elements 34 are selected from the group consisting of metals, ceramics, and mixtures thereof. Preferred metals include, titanium, tantalum, steel, platinum, gold, palladium, and combinations thereof. Preferred ceramics include metal oxides, such as alumina ($Al_2O_3$), zirconia ($ZrO_2$), and magnetite ($Fe_3O_4$). In addition, individual MRI-imageable elements 34 may each comprise a plurality of different materials, such as an alloy. The use of a plurality of MRI-imageable elements 34 allows site marker 12 to be customized to particular imaging procedures and devices by adjusting the composition, amount, size, shape, and/or spatial distribution of MRI-imageable elements 34. For example, for an MRI device with a relatively strong magnetic field, the number of MRI-imageable elements 34 may be reduced so that the magnetic field does not displace site marker 24 within the patient's anatomy, whereas for an MRI device with a relatively weaker magnetic field, the number of MRI-imageable elements 34 may be increased to ensure that site marker 12 is sufficiently visible on an MR image.

Figure 3B:
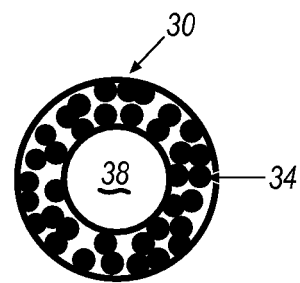
FIG. 3B is a cross-sectional view of the site marker of FIG. 2 taken along line 3-3 in accordance with an alternative embodiment of a site marker.

Referring to FIG. 3B, an alternative embodiment of a site marker is depicted. In accordance with the embodiment, site marker 12 includes radiopaque element 30 with MRI-imageable elements 34 suspended within the material comprising radiopaque element 30 to define a solid mixture. In FIG. 3B, site marker 12 is in the shape of an annulus with a hollow interior 38. The cross-sectional thickness of the annulus has been exaggerated to better depict MRI-imageable elements 34. Site marker 12 may also comprise a solid body with no hollow interior or void spaces. MRI-imageable elements 34 may be uniformly or non-uniformly distributed throughout any or all of the dimensions (e.g., length, width, height, radius) of the radiopaque material comprising radiopaque element 30. In addition, MRI-imageable elements 34 may have the same or different, sizes, shapes, and/or compositions. In one implementation, the MRI-imageable elements 34 are combined with the radiopaque material while the radiopaque material is in a molten state to form site marker 12. If the radiopaque material is provided as a granular material and heated to create a molten state, the MRI-imageable elements 34 may also be combined with the granular material prior to heating. The mixture of radiopaque material and MRI-imageable elements 34 is then heated to a molten state and solidified, such as by cooling.

In the embodiment of FIG. 3B, MRI-imageable elements 34 may be tightly packed within the radiopaque material so as to abut adjacent elements 34 or they may be spaced apart from one another along any or all of the dimensions of site marker 12. In addition, MRI-imageable elements 34 may define certain regions in which they are tightly packed and others in which they are spaced apart from one another, thereby defining a non-uniform spatial distribution. As with the previous embodiment, the compositions, sizes, shapes, distribution, and/or number of MRI-imageable elements 34 are preferably selected to provide the required degree of magnetic sensitivity in the MRI device and procedure that are being used.

As is known to those skilled in the art, magnetic resonance spectroscopy ("MRS") is a procedure that can be used to obtain information about the chemical content of tissue regions of interest, such as breast lesions. In MRI, the absorbed RF signal is used to create an image. However, in MRS, the absorbed RF signals are used to create a spectrum that is indicative of the presence of different groups of atoms surrounding a specific nucleus (e.g., $^{31}P$, $^1H$, $^{13}C$, $^{23}Na$). Proton MRS (i.e., the nucleus is $^1H$) is preferred. As is known to those skilled in the art, metabolites have one or more defined chemical shift values (ppm) on a magnetic resonance spectrum. For example, alanine has a shift of 1.47 ppm, N-acetylaspartate has shifts of 2.0 and 2.6 ppm, creatine has a shift of 3.0 and 3.9 ppm, water has a shift of 5.0 ppm, and choline has shifts of 3.2 ppm. It has been found that choline levels may be used to distinguish malignant from benign lesions. Bolan, et al., "Imaging in Breast Cancer: Magnetic Resonance Spectroscopy," *Breast Cancer Research* 2005, 7:149-152 and Nofray, U.S. Pat. No. 7,289,840. However, certain metallic site markers may interfere with the choline spike in an MRS spectrum. Thus, for applications in which MRS is contemplated, site marker 12 is preferably selected to be visible under MRI and MRS compatible.

In certain illustrative embodiments, MRI-imageable elements 34 comprise one or more metals having a composition, size, shape, distribution, and/or number that allows site marker 12 to be both MRI-imageable and MRS-compatible. In other illustrative embodiments, MRI-imageable elements 34 comprise ceramic materials, such as one or more of the metal oxides described above, having a composition, size, shape, distribution, and/or number that provides MRS-compatibility. As used herein, the term "MRS compatible" means that the materials do not distort the MRS spectrum. In those embodiments wherein MRS is performed to determine whether a lesion is benign or malignant, the MRI-imageable elements preferably do not distort at least the choline peak of the MRS spectrum.

In certain embodiments, MRI-imageable elements 34 may comprise multiple groups of elements, each of which differs in its ability to be visualized under different imaging modalities. For example, MRI-imageable elements 34 may comprise metal elements in one portion of radiopaque element 30 and ceramic elements in another portion of radiopaque element 30. In another example, different metals may be used in different portions of radiopaque element 30. In yet another example, multiple types of metals and/or ceramics may comprise MRI-imageable elements 34. The use of multiple types (e.g., multiple compositions, sizes, shapes) of MRI-imageable elements provides variable imaging properties along the different dimensions (e.g., length and width or diameter) of radiopaque element 30. In still another embodiment, the spatial distribution of MRI-imageable elements within radiopaque element 30 may be uniform or non-uniform. In one example of a non-uniform distribution, two groups of MRI-imageable elements 34 may be included in radiopaque element 30 and spaced apart from one another. The composition, size, number, shape, and spatial distribution of each group of MRI-imageable elements 34 may be selectively adjusted to achieve a desired degree of visualization under specific imaging modalities. Different MRI-imageable elements 34 may be used which differ in their ability to be visualized under certain modalities or in their compatibility with certain modalities. However, they also may differ in the degree to which they can be visualized in any one modality.

A method of using site marker 12 to identify the location of a biopsied tissue specimen will now be described. In accordance with the method, site marker 12 is provided as described in the foregoing embodiments. A suspected cancerous mass is located in the patient, and a tissue sample is removed from the identified location. The site marker 12 is then implanted at the location. The patient may then be x-rayed in the area of the body surrounding the location and the location of the site marker 12 may be identified on the x-ray image. In addition, the patient may be subjected to MRI, and the site marker 12 may be identified on the MRI image. Either or both of the x-ray and MRI images may then be examined to determine whether there is any tumor growth at the biopsy site. If necessary, the patient may be re-biopsied at the biopsy location or may undergo a lumpectomy by correlating locations on the patient's anatomy to the site marker location on either or both of the x-ray image and the MRI image. In certain preferred embodiments, the site marker 12 is implanted by inserting site marker delivery system 20 through the inner lumen of a biopsy device (not shown) to better ensure that the site marker 12 is implanted at the location from which the biopsy sample was taken.

It may be desirable to further obtain a MRS spectrum of the tissue in the area of the biopsy site to determine the levels of chemical entities indicative of cancer. In a preferred embodiment, MRI-imageable elements 34 are selected in the manner described above to provide an MRI-compatible site marker 12, and an MRS spectrum is obtained following implantation of site marker 12. The choline shift is then evaluated to determine whether cancerous cells may be developing or increasing in number. In certain embodiments, a baseline choline level is obtained from an MRS spectrum prior to applying a therapeutic treatment (e.g., chemotherapy or a lumpectomy) and a follow up spectrum is obtained to identify relative changes in the choline level proximate site marker 12.

It will be appreciated that site markers and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed as new and desired to be protected by Letters Patent of the United States is:

1. A site marker, comprising:
   a radiopaque element defining an outer shell of the site marker, wherein the outer shell defines a hollow cavity and is formed of a bio-compatible material that is not imageable using magnetic resonance imaging; and
   a plurality of marker elements disposed within the hollow cavity, wherein the marker elements are formed of a material that is imageable using magnetic resonance imaging, and wherein the marker elements move freely within the hollow cavity.

2. The site marker of claim 1, wherein the radiopaque element is comprised of a glass material.

3. The site marker of claim 1, wherein the plurality of marker elements are made of metal.

4. The site marker of claim 1, wherein the plurality of marker elements are made of ceramic.

5. The site marker of claim 1, wherein the plurality of marker elements are made of a non-metal material.

6. The site marker of claim 1, wherein the plurality of marker elements are uniformly shaped.

7. The site marker of claim 1, wherein the plurality of marker elements have a uniform composition.

8. The site marker of claim 1, wherein the plurality of marker elements are uniformly spaced along at least one dimension of the site marker.

9. The site marker of claim 1, wherein the site marker is imageable using magnetic resonance imaging and is compatible with a magnetic resonance spectroscopy spectrum.

10. The site marker of claim 1, wherein at least one of a number of the marker elements, a composition of the marker elements, a size of the marker elements, a shape of the marker elements, a spatial distribution of the plurality of marker elements, and a shape of the outer shell is selected based on a predetermined imaging procedure.

* * * * *

UNITED STATES PATENT AND TRADEMARK OFFICE
CERTIFICATE OF CORRECTION

| | | |
|---|---|---|
| PATENT NO. | : 8,433,391 B2 | Page 1 of 1 |
| APPLICATION NO. | : 12/269501 | |
| DATED | : April 30, 2013 | |
| INVENTOR(S) | : Joseph L. Mark | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 237 days.

Signed and Sealed this
Fourth Day of November, 2014

Michelle K. Lee
*Deputy Director of the United States Patent and Trademark Office*